Figure 1A:
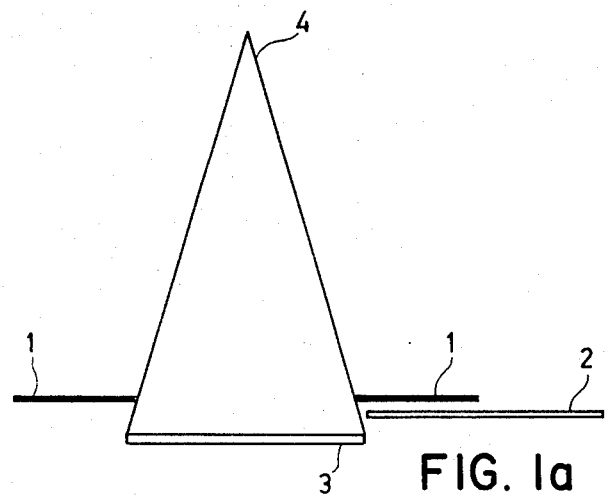

United States Patent [19]
Kunert

[11] 3,975,642
[45] Aug. 17, 1976

[54] IMAGE SECTION OF AN X-RAY APPARATUS

[75] Inventor: Heinz-Peter Kunert, Tangstedt, Germany

[73] Assignee: U.S. Philips Corporation, New York, N.Y.

[22] Filed: Jan. 27, 1975

[21] Appl. No.: 544,350

Related U.S. Application Data
[63] Continuation of Ser. No. 373,507, June 25, 1973, abandoned.

[30] Foreign Application Priority Data
July 1, 1972 Germany............................ 2232413

[52] U.S. Cl................................. 250/468; 250/511
[51] Int. Cl.²........................................ G03B 41/16
[58] Field of Search ........... 250/468, 469, 470, 471, 250/511, 512, 513, 514

[56] References Cited
UNITED STATES PATENTS

| 2,257,050 | 9/1941 | Goldfield | 250/514 |
| 2,921,202 | 1/1960 | Berger | 250/468 |
| 3,130,313 | 4/1964 | Tilling | 250/511 |
| 3,614,427 | 10/1971 | Vacher | 250/320 |

*Primary Examiner*—Craig E. Church
*Attorney, Agent, or Firm*—Frank R. Trifari; Ronald L. Drumheller

[57] ABSTRACT

The invention relates to an image section of an X-ray apparatus for medical applications, comprising a control unit which completely or partly closes the diaphragm during the movement of the cassette from the parking position to the recording position. This prevents fogging which can otherwise occur when the film is exposed during this movement of the cassette to the slowly disappearing X-radiation caused by preceding fluoroscopy.

2 Claims, 6 Drawing Figures

IMAGE SECTION OF AN X-RAY APPARATUS

This is a continuation of application Ser. No. 373,507 filed June 25, 1973, now abandoned.

The invention relates to the image section, for example, the series cassette, of an X-ray apparatus comprising a display screen and a carriage which contains the film and which can be moved from a parking position which is situated outside the beam path, to a recording position which is situated inside the beam path which is directed to the display screen, and also comprising an adjustable diaphragm for adjusting the cross-section of the beam. Image sections of this kind are known.

A requirement for medical applications is that the image section should be constructed such that the time expiring between the end of fluoroscopy displayed on the display screen and the beginning of subsequent recording is as short as possible, so that fast processes observed on the display screen, for example, deglutitions, can be recorded on the film.

In order to satisfy this requirement, it is proposed (German Pat. No. 2,002,634) to arrange the movable carriage with the film each time such that (in the case of movement from right to left) the left-hand side of the carriage is situated as near as possible to the beam which is limited by the diaphragm. As a result, the distance to be travelled by the carriage so as to reach the recording position from the parking position is minimized.

However, the theoretically feasible reduction of the time interval between the end of fluoroscopy and the beginning of recording (= preparation time) cannot be completely realized, because even though the high voltage for the X-ray tube is automatically switched off in modern X-ray apparatus at the beginning of the preparation time, the X-radiation does not immediately decrease to zero. This is due to the capacitances of the high voltage cables for the X-ray tube and to any capacitances present in the high voltage generator, and also due to the fact that the filament voltage is not switched off, but is even increased for recording, so that the capacitances can be discharged via the X-ray tube, thus producing X-rays. The duration of the disappearing eventually post-radiation is particularly long after fluoroscopy in a unfavourable case some tenths of a second - because the anode current of the tube is comparatively small during fluoroscopy - and also thereafter — so that the charges leak away only very slowly. If the film has already reached the beam path during this period, the film is already blackened before the recording, — be it to a comparatively small extent in view of the low intensity of the post-radiation —, with the result that a fog is superimposed on the subsequent recording.

So as to avoid such fogging, the carriage would have to be brought into the beam path only after disappearance of the post-radiation. However, this contradicts the requirement that the cassette must be brought into the recording position as quickly as possible.

The invention has for its object to provide an image section of an X-ray apparatus in which the described fogging is avoided, whilst the carriage can still be brought into the beam path without delay.

This is achieved in that control means are provided which control the diaphragm during the movement of the carriage from the parking position to the recording position such that the post-radiation is shielded from the moving carriage and hence from the film, and which immediately thereafter automatically set the diaphragm for recording.

Figure 1B:
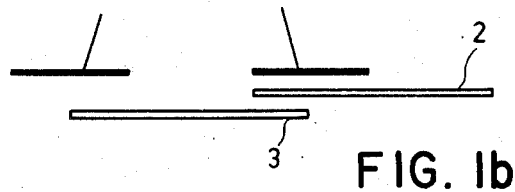
Figure 1C:
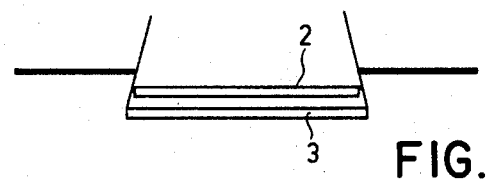
Figure 3A:
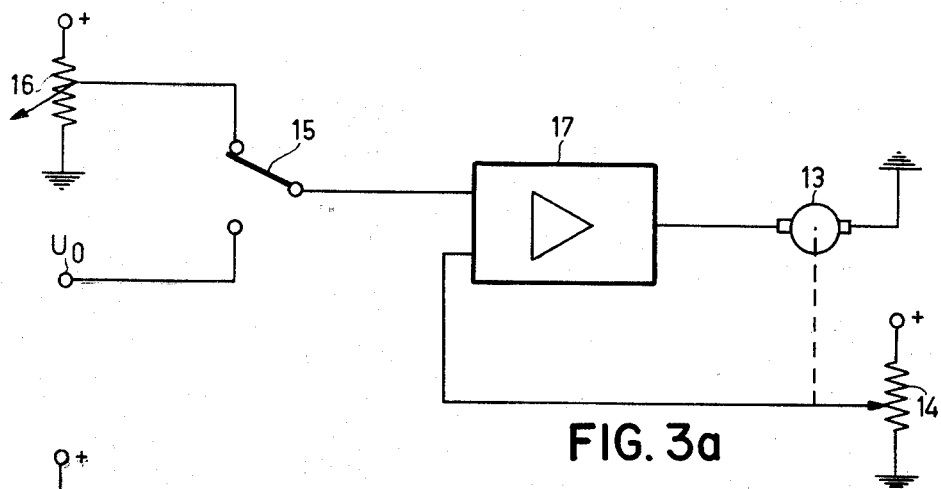
Figure 3B:
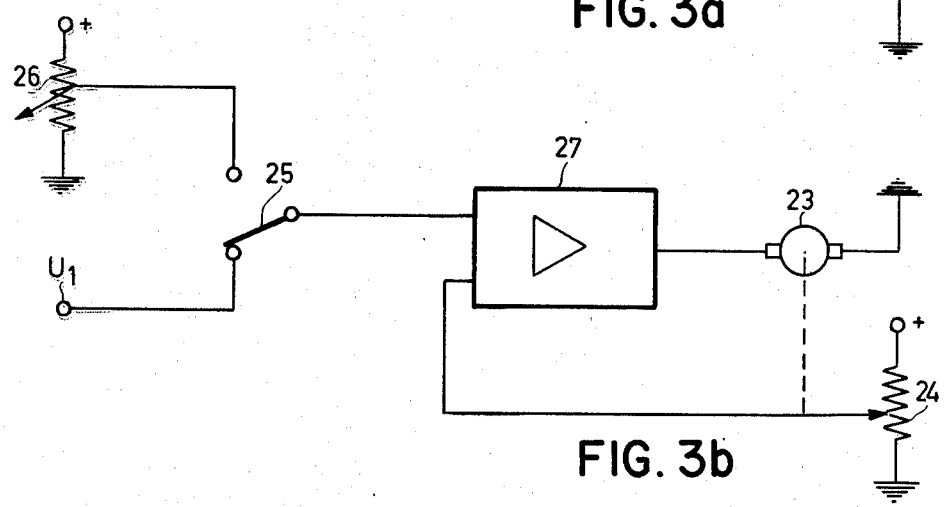
Figure 2:
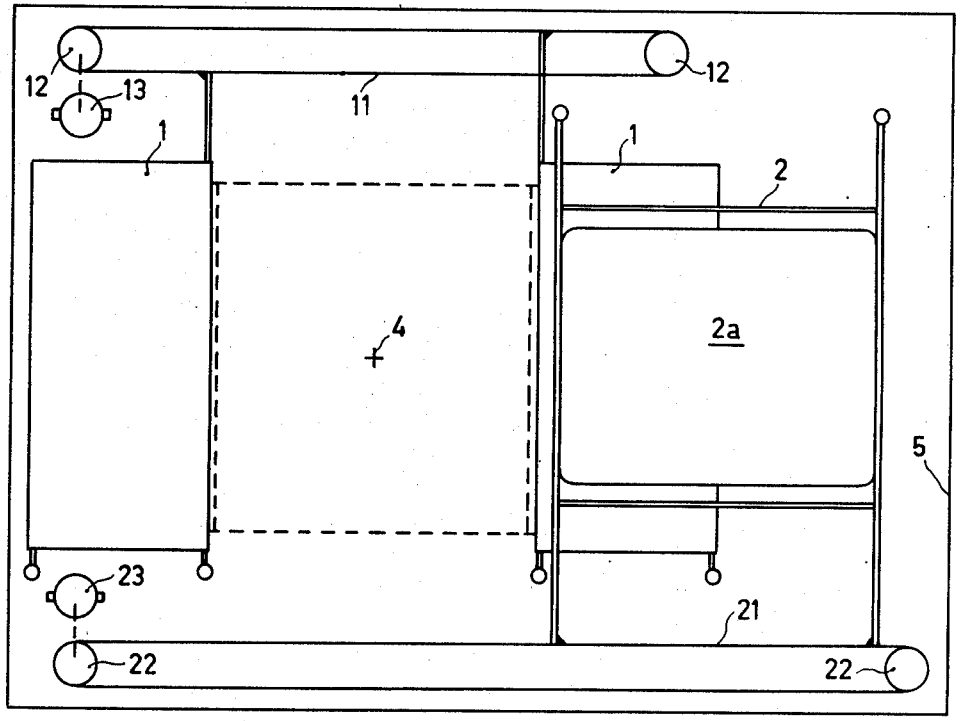

The invention will now be described in detail with reference to the accompanying drawing, in which FIG. 1 shows the setting of the diaphragm and the position of the carriage at the beginning (FIG. 1a), during (FIG. 1b), and at the end (FIG. 1c) of the preparation time, whilst FIGS. 2, 3a and 3b, diagrammatically show an embodiment according to the invention.

FIG. 1a is a diagrammatic representation of the setting of a diaphragm 1 which consists of two diaphragm laminations and which is arranged near the film, and of the position of the carriage 2 and the display screen 3 with respect to a beam originating from a radiation source 4, the boundaries of the said beam being denoted in the drawing, at the beginning of the preparation time. The carriage 2 is still in the parking position in which it is protected from X-radiation by a lead cover in the image section (not shown). Moreover, the diaphragm laminations 1 bound the beam such that only the display screen is exposed to the radiation.

FIG. 1b shows the setting of the diaphragm and the position of the carriage during the preparation time. The carriage is then already partly situated within the boundary lines of the beam and the film would be exposed if the diaphragm laminations had not in the meantime been moved towards each other, thus screening the film. The diaphragm laminations 1 must be moved towards each other at least so far that during the movement of the carriage no radiation can be incident on the film or the carriage. However, they can alternatively be fully closed. When the carriage has reached the recording position or when the radiation has disappeared, the diaphragm laminations are returned to the position required for recording, as is shown in FIG. 1c. Recording can subsequently take place.

FIG. 2 shows the diaphragm 1 and the carriage 2, comprising a cassette 2a containing the film, as part of the image section 5, only the frame and the parts which are essential for the description of the invention being shown in the drawing. The cassette carriage 2 is in the parking position, outside the beam path which is denoted by the broken lines and the centre 4 of the X-ray tube. In this position no radiation can be incident on the carriage. The displacement of the carriage from the parking position to the recording position is effected by means of a motor 23 which drives one of the pulleys 22 on which a belt 21 is transported which is rigidly connected to the carriage 2.

The diaphragm 1 is arranged near the film and is set by means of a motor 13 which drives one of the pulleys 12 on which a belt 11 is transported. The left-hand diaphragm lamination is connected to the part of the belt which is transported below the pulleys, whilst the right-hand diaphragm lamination is connected to the part of the belt which is transported over the pulleys, with the result that the two diaphragm laminations are always moved in an opposite sense.

The displacement of the carriage 2 and the setting of the diaphragm 1 can be effected by means of a servo system, as is shown in FIG. 3. The motor 13 (23) then displaces the slide contact of a potentiometer 14 (24) until the (actual) direct voltage derived therefrom is equal to a (desired) direct voltage which is compared on the input of a switching amplifier 17 (27) with the (actual) direct voltage. When the voltage difference has approximately reached the value zero, the current to the motor 13 (23) which is connected to the output of the switching amplifier 17 (27) is interrupted, and the motor stops. As the motor 13 (23) drives both the potentiometer slide contact 14 (24) and the pulleys 12 (22), the position reached after the switching-off of the motor depends on the (desired) direct voltage on the input of the switching amplifier. The setting distance of the diaphragm, or the displacement distance of the carriage, can thus be adjusted by selecting the desired direct voltage.

At the beginning of the preparation time, the input for the desired direct voltage of the switching amplifier 27 is switched over by means of a switch 25 from a voltage $U_t$, corresponding to the parking position, to the voltage on the slide contact of a potentiometer 26. The slide contact of the potentiometer 26 is adjusted such that the motor 23 is automatically switched off when the carriage 2 reaches the recording position.

Simultaneously with this switch-over, the desired direct voltage on the input of the switching amplifier 17, controlling the motor 13 for setting the diaphragm, is switched over from the voltage on the slide contact of a potentiometer 16, corresponding to the recording position of the diaphragm, to a voltage $U_o$ by means of a switch 15, so that the diaphragm 1 performs a closing movement.

The voltage $U_o$ can be selected such that the diaphragm 1 is fully closed. In that case the carriage 2 can reach the recording position before the post-radiation has completely disappeared. However, the diaphragm 1 need not be completely closed. It is sufficient to select the voltage $U_o$ such that the post-radiation has disappeared when the side of the cassette 2a which faces the beam path moves past the corresponding side of the right-hand diaphragm lamination in the direction of the recording position. The voltage $U_o$ and the drive speeds of the servo control system, consequently, must always be chosen such that the carriage cannot be exposed to the post-radiation during its displacement.

For the resetting of the switch 15, use can be made of a timing member (not shown) which initiates the switchover after expiration of a period which corresponds to the longest duration of the post-radiation. The switch-over can also be performed in dependence of the direct voltage difference on the input of the switching amplifier 27, i.e. such that the switch-over is initiated when the voltage difference disappears (i.e. when the cassette has reached the recording position). If the switch-over takes place after the carriage has reached the recording position but before the post-radiation has completely disappeared, the stationary film is exposed to the post-radiation but there will be no out-of-focus effects because the situation of the organs to be recorded is generally not changed for the remainder of the duration of the post-radiation and the recording. Consequently, the time for transporting the cassette from the parking position to the recording position can be made shorter than the duration of the post-radiation.

Instead of being screened by the diaphragm which is arranged in the vicinity of the film in the image section, the film can alternatively be screened during the movement of the carriage towards the recording position by a diaphragm which is remote from the film and which is connected to the X-ray tube. However, it must then be taken into account that the distance between the X-ray tube and the image section is variable, with the result that the position until which the diaphragm must at least be closed must also be varied. This can be effected by a corresponding variation of the voltage $U_o$ (for example, by means of a potentiometer); however, the diaphragm can alternatively be fully closed during this movement of the carriage, so that variations of the said distance need not be taken into account.

What is claimed is:
1. A method of more quickly positioning X-ray film for exposure followng interruption of fluoroscopy, comprising the steps of:
   simultaneously with interruption of fluoroscopy, closing a diaphragm positioned between the film exposing area and the X-ray tube to block post-radiation from said area;
   at the same time, moving X-ray film into said exposing area at a lower speed, so that post-radiation is screened from said film by said diaphragm; and
   when there is no longer any danger of exposing moving film to post-radiation, opening said diaphragm.

2. X-ray machine apparatus for moving X-ray film into recording position immediately following interruption of fluoroscopy without fogging said film with post-radiation, comprising:
   means for making fluoroscopic examinations
   a film carriage displaceable from a parking position outside the X-ray beam path to a recording position within the X-ray beam path;
   a first servo system for driving said film carriage from said parking position to said recording position immediately following interruption of fluoroscopy;
   an adjustable diaphragm having an aperture defining the cross-section of the X-ray beam during fluoroscopy; and
   a second servo system for automatically reducing the aperture of said diaphragm, as said carriage moves toward said recording position, at a rate sufficient and for a length of time sufficient to assure that film carried by said moving carriage is screened by said diaphragm from post-radiation.

* * * * *